(12) United States Patent
Yun

(10) Patent No.: US 9,051,532 B1
(45) Date of Patent: Jun. 9, 2015

(54) ORGANOLEPTIC COMPOUND

(71) Applicant: International Flavors & Fragrances Inc., New York, NY (US)

(72) Inventor: Heedong Yun, Tenafly, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 14/287,601

(22) Filed: May 27, 2014

(51) Int. Cl.
    *C11B 9/00*     (2006.01)
    *C11D 3/50*     (2006.01)
    *C07C 403/08*     (2006.01)

(52) U.S. Cl.
    CPC ............... *C11B 9/0034* (2013.01); *C11D 3/50* (2013.01); *C07C 403/08* (2013.01); *C07C 2101/16* (2013.01)

(58) Field of Classification Search
    CPC ..................... C07C 2101/16; C07C 403/08
    USPC .............................. 568/826, 823, 822
    See application file for complete search history.

(56) References Cited

U.S. PATENT DOCUMENTS 4,250,342 A * 2/1981 Sprecker et al. ............... 568/826
4,283,576 A * 8/1981 Sprecker et al. ............... 568/826

* cited by examiner

*Primary Examiner* — Elvis O Price
(74) *Attorney, Agent, or Firm* — Xufan Tseng; Martin Z. Zhang; Elizabeth M. Quirk

(57) ABSTRACT

The present invention is directed to a novel compound, 1-(2, 4-dimethyl-cyclohex-3-enyl)-propan-1-ol, and a method of improving, enhancing or modifying a fragrance formulation through the addition of an olfactory acceptable amount of 1-(2,4-dimethyl-cyclohex-3-enyl)-propan-1-ol.

9 Claims, No Drawings

ORGANOLEPTIC COMPOUND

FIELD OF THE INVENTION

The present invention relates to a novel compound and its incorporation and use as a fragrance material.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

SUMMARY OF THE INVENTION

The present invention provides a novel compound 1-(2,4-dimethyl-cyclohex-3-enyl)-propan-1-ol and its unexpected advantageous use in enhancing, improving or modifying the fragrance of perfumes, colognes, toilet waters, personal products, fabric care products, and the like.

One embodiment of the present invention is directed to 1-(2,4-dimethyl-cyclohex-3-enyl)-propan-1-ol, a novel fragrance compound, represented by the following formula:

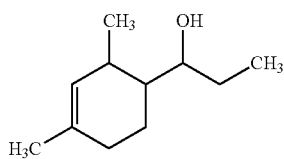

Structure I

Another embodiment of the present invention is directed to the use of 1-(2,4-dimethyl -cyclohex-3-enyl)-propan-1-ol as a fragrance material in perfumes, colognes, toilet waters, personal products, fabric care products, and the like.

Another embodiment of the present invention is directed to a fragrance composition comprising 1-(2,4-dimethyl-cyclohex-3-enyl)-propan-1-ol.

Another embodiment of the present invention is directed to a fragrance product comprising 1-(2,4-dimethyl-cyclohex-3-enyl)-propan-1-ol.

Another embodiment of the present invention is directed to a method of improving, enhancing or modifying a fragrance formulation by incorporating an olfactory acceptable amount of 1-(2,4-dimethyl-cyclohex-3-enyl)-propan-1-ol.

These and other embodiments of the present invention will be apparent by reading the following specification.

DETAILED DESCRIPTION OF THE INVENTION

It has been surprisingly found that 1-(2,4-dimethyl-cyclohex-3-enyl)-propan-1-ol possesses unexpected powerful and complex notes with a unique clean, fresh and floral combination.

1-(2,4-Dimethyl-cyclohex-3-enyl)-propan-1-ol of the present invention is represented by the following structure:

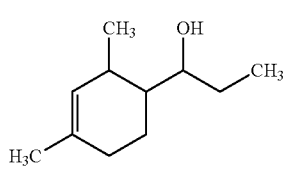

Structure I 1-(2,4-Dimethyl-cyclohex-3-enyl)-propan-1-ol can be prepared according to the following reaction scheme, the details of which are specified in the Examples. The reagents were purchased from Aldrich Chemical Company unless noted otherwise.

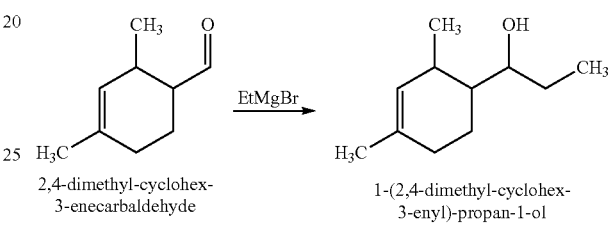

2,4-dimethyl-cyclohex-3-enecarbaldehyde 1-(2,4-dimethyl-cyclohex-3-enyl)-propan-1-ol Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The use of the compound of the present invention is widely applicable in current perfumery products, including the preparation of perfumes and colognes, the perfuming of personal care products such as soaps, shower gels, and hair care products, fabric care products as well as air fresheners and cosmetic preparations. This compound can also be used to perfume cleaning agents, such as, but not limited to detergents, dishwashing materials, scrubbing compositions, window cleaners and the like. In these preparations, the compound of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk; and flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety, Another source of suitable fragrances is found. in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compound of the present invention can be used in combination with a complementary fragrance compound. The term "complementary fragrance compound" as used herein is defined as a fragrance compound selected from the group consisting of 2-[(4-methylphenyl)methytene]-heptanal (Acalea), iso-amyl oxyacetic acid allylester (Allyl Amyl Glycolate), (3,3-dimethylcyclohexyl)ethyl ethyl propane-1, 3-dioate (Applelide), 2-ethyl-4-(2,2,3-trimethyl-3-cyclopenten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro -1,1,2,3,3-pentamethyl-4H-inden-4-one (Cashmeran), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano -1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4 -ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4, 6,7,8-hexahydro-4,6,6,7,8,8-hexamethylcyclopenta-gamma-2-benzopyran (Galaxolide), 1-(5,5-dimethyl-1-cyelohexen-1-yl)pent-4-en-1-one (Galbascone), E/Z-3,7 -dimethyl-2,6-octadien-1-yl acetate (Geranyl Acetate) α-methyl-1,3-benzodioxol-5-propanal (Helional), 1-(2,6,6-trimethyl-2-cyclohexen-1-yl)-1,6-heptadien-3-one (Hexalon), (Z)-3-hexenyl -2-hydroxybenzoate (Hexenyl Salicylate, CIS-3), 4-(2,6,6-trimethyl-2-cyclohexen-1-yl)-3-buten -2-one (Ionone α), 1-(1,2,3,4,5,6,7,8-octahydro-2,3,8, 8-tetramethyl-2-naphthalenyl)-ethan-1-one (Iso E Super), methyl 3-oxo-2-pentylcyclopentaneacetate (Kharismal), 2,2, 4-trimethyl-4-phenyl -butanenitrile (Khusinil), 3,4,5,6,6-pentamethylhept-3-en-2-one (Koavone), 3/4-(4-hydroxy-4 -methyl-pentyl) cyclohexene-1-carboxaldehyde (Lyral), 3-methyl-4-(2,6,6-trimethyl-2 -cyclohexen-1-yl)-3-buten-2-one (Methyl Ionone γ), 1-(2,6,6-trimethyl-2-cyclohexen-1-yl) pent-1 -en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13 -dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3 -methyl-5-phenylpentanol (Phenoxanol), 1-methyl-4-(4-methyl-3-pentenyl) cyclohex-3-ene-1 -carboxaldehyde (Precyclemone B), 2-ethyl-4-(2,2,3-trimethyl-3-cyclopenten-1-yl)-2-buten-1-ol (Sanjinol), 2-methyl-4-(2, 2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H -indeno[4, 5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl) oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention may comprise a compound of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention. The fragrance product of the present invention may contain a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the compound of the present invention employed in a fragrance formulation varies from about 0.005 to about 50 weight percent, preferably from 0.1 to about 25 weight percent, and more preferably from about 0.5 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides clean, fresh and floral notes that make the fragrance formulation more desirable and noticeable and add the perception of value. All of the odor qualities found in this material assist in beautifying and enhancing the finished accord improving the performance of the other materials in the fragrance. The fruity side is found in many fragrances today which happens to be very trendy, especially for the younger consumers.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, M is understood to be molar, L is understood to be liter, g be gram and Kg is understood to be kilogram. IFF as used in the examples is understood to mean International Flavors & Fragrances Inc., New York, N.Y., USA.

EXAMPLE I

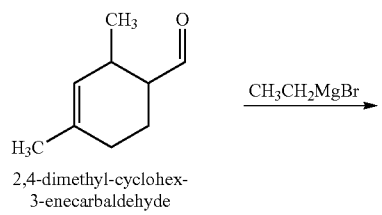

2,4-dimethyl-cyclohex-3-enecarbaldehyde 1-(2,4-dimethyl-cyclohex-3-enyl)-propan-1-ol Preparation of 1-(2,4-Dimethyl-cyclohex-3-enyl)-propan-1-ol (Structure I):

A reaction flask was charged with ethylmagnesium bromide solution ($CH_3CH_2MgBr$) (3 M, 2.4 L) in tetrahydrofuran (THF) and cooled to 0° C. 2,4-Dimethyl-cyclohex-3-enecarbaldehyde (905 g) was added slowly while the temperature was kept at 0° C. The reaction mixture was stirred for an additional hour and then quenched with hydrochloric acid (HCl). The reaction mixture was washed with sodium carbonate ($Na_2CO_3$) and brine. Further distillation provided 1-(2,4-dimethyl-cyclohex-3-enyl)-propan-1-ol (1.021 Kg).
$^1$H NMR ($CDCl_3$, 400 MHz): 5.44-5.18 ppm (m, 1H), 3.76-3.33 ppm (m, 1H), 2.48-0.89 ppm (m, 9H), 1.64 ppm (s, 3H), 0.96 ppm (t, 3H, J=7.00 Hz), 0.85 ppm (d, 3H, J=6.97)

EXAMPLE II

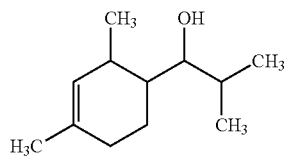

1-(2,4-dimethyl-cyclohex-3-enyl)-ethanol

Preparation of 1-(2,4-Dimethyl-cyclohex-3-enyl)-ethanol (Structure II):

1-(2,4-Dimethyl-cyclohex-3-enyl)-ethanol was similarly prepared.
$^1$H NMR ($CDCl_3$, 500 MHz): 5.14-5.45 ppm (m, 1H), 3.46-4.03 ppm (m, 1H), 1.57-2.53 ppm (m, 4H), 1.63 ppm (s, 3H), 1.03-1.54 ppm (m, 6H), 0.80-1.03 ppm (m, 3H)

EXAMPLE III

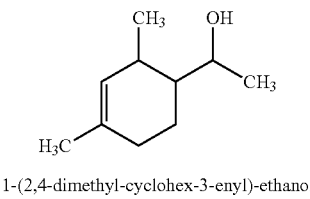

1-(2,4-dimethyl-cyclohex-3-enyl)-butan-1-ol

Preparation of 1-( 2,4-Dimethyl-cyclohex-3-enyl)-butan-1-ol (Structure III):

1-(2,4-Dimethyl-cyclohex-3-enyl)-butan-1-ol was similarly prepared.
$^1$H NMR ($CDCl_3$, 360 MHz): 5.10-5.45 ppm (m, 1H), 3.25-3.80 ppm (m, 1H), 1.64 ppm (s, 3H), 0.70-2.50 ppm (m, 17H)

EXAMPLE IV

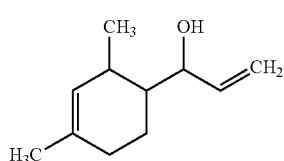

1-(2,4-dimethyl-cyclohex-3-enyl)-2-methyl-propan-1-ol

Preparation of 1-(2,4-Dimethyl-cyclohex-3-enyl)-2-methyl-propan-1-ol (Structure IV):

1-(2,4-Dimethyl-cyclohex-3-enyl)-2-methyl-propan-1-ol was similarly prepared.
$^1$H NMR ($CDCl_3$, 500 MHz): 5.15-5.53 ppm (m, 1H), 3.06-3.67 ppm (m, 1H), 1.67-2.50 ppm (m, 5H), 1.64 ppm (s, 3H), 1.21-1.63 ppm (m, 3H), 0.71-1.07 ppm (m, 9H)

EXAMPLE V

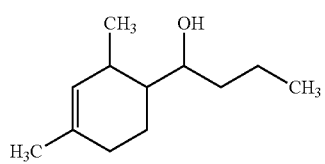

1-(2,4-dimethyl-cyclohex-3-enyl)-pentan-1-ol

Preparation of 1-(2,4-Dimethyl-cyclohex-3-enyl)-pentan-1-ol (Structure V):

1-(2,4-Dimethyl-cyclohex-3-enyl)-pentan-1-ol was similarly prepared.
$^1$H NMR ($CDCl_3$, 360 MHz): 5.01-5.48 ppm (m, 1H), 3.19-3.95 ppm (m, 1H), 1.64 ppm (s, 3H), 0.75-2.50 ppm (m, 19H)

EXAMPLE VI 1-(2,4-dimethyl-cyclohex-3-enyl)-prop-2-en-1-ol

Preparation of 1-(2,4-Dimethyl-cyclohex-3-enyl)-prop-2-en-1-ol (Structure VI):

1-(2,4-Dimethyl-cyclohex-3-enyl)-prop-2-en-1-ol was similarly prepared.
$^1$H NMR ($CDCl_3$, 500 MHz): 5.80-6.02 ppm (m, 1H), 5.13-5.36 ppm (m, 3H), 3.80-4.35 ppm (m, 1H), 1.69-2.55 ppm (m, 5H), 1.64 ppm (s, 3H), 1.18-1.61 ppm (m, 2H), 0.81-1.05 ppm (m, 3H)

EXAMPLE VII

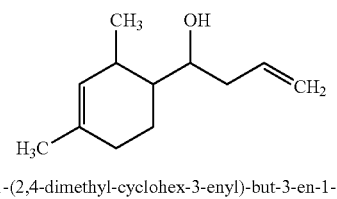

1-(2,4-dimethyl-cyclohex-3-enyl)-but-3-en-1-ol

Preparation of 1-(2,4-Dimethyl-cyclohex-3-enyl)-but-3-en-1-ol (Structure VII):

1-(2,4-Dimethyl-cyclohex-3-enyl)-but-3-en-1-ol was prepared according to the disclosure of U.S. Pat. No. 4,195,099.

EXAMPLE VIII

The fragrance properties of the above compounds (i.e., Structures I-VII) were evaluated using (i) odor strength of 0 to 10, where 0=none, 1=very weak, 5=moderate, 10=extremely strong; and (ii) level of complexity, where 0=none, 1=very low, 5=moderate, 10=extremely high, Averaged scores are reported in the following:

| Chemical Name | Compound | Odor Profile | Strength | Complexity |
| --- | --- | --- | --- | --- |
| 1-(2,4-Dimethyl-cyclohex-3-enyl)-propan-1-ol (Structure I) | | Clean and fresh notes with unique rosy character and eucalyptus, spicy and herbaceous background. The spiciness provided additional dimension and further floralcy of geranium, natural and green provided complexity. | 9 | 10 |
| | | Odor quality maintained when prepared in 5% ethanol solution. Clean and fresh notes with rosy, herbaceous and geranium characters. Complex but natural with delicate and sensual feel. | 8 | 10 |
| 1-(2,4-Dimethyl-cyclohex-3-enyl)-ethanol (Structure II) | | Green, gassy and hay-like notes with a styrene (plastic)-like, oily and chemical quality. | 4 | 4 |
| | | Less powerful when prepared in 5% ethanol solution. The top notes became woody and less complex. The chemical quality remained. | 3 | 3 |
| 1-(2,4-Dimethyl-cyclohex-3-enyl)-butan-1-ol (Structure III) | | Fruity note with anisic and onion-like quality. | 2 | 2 |
| | | The anisic quality became stronger when prepared in 5% ethanol solution. The onion-like character remained. | 2 | 2 |
| 1-(2,4-Dimethyl-cyclohex-3-enyl)-2-methyl-propan-1-ol (Structure IV) | | Fresh, floral and woody notes with citrus quality. The woodiness provided complexity with vetivert-like quality. The pine-like and soapy characters yielded the impression of a floor cleaner. Overall odor was chemical. | 5 | 5 |
| | | Fresh when prepared in 5% ethanol solution but a dirty note developed when dried. | 4 | 3 |

-continued

| Chemical Name | Compound | Odor Profile | Strength | Complexity |
|---|---|---|---|---|
| 1-(2,4-Dimethyl-cyclohex-3-enyl)-pentan-1-ol (Structure V) | | Lilac and muguet-like floralcy but simple and weak. Woody note with weak, chemical and dirty characters. | 2 | 2 |
| | | Much weaker and more chemical when prepared in 5% ethanol solution. Floralcy was lost. Green note without strength and complexity. | 2 | 2 |
| 1-(2,4-dimethyl-cyclohex-3-enyl)-prop-2-en-1-ol (Structure VI) | | Oily and chemical top notes with reminiscent of clay and chemical quality. Interesting tomato leaf-like character but without complexity. | 4 | 3 |
| | | Oily, slightly fishy and amine-like notes when prepared in 5% ethanol solution. Artificial green note without strength and complexity. | 3 | 3 |
| 1-(2,4-Dimethyl-cyclohex-3-enyl)-but-3-en-1-ol (Structure VII) | | Fresh note with spicy and herbaceous quality supported by further floralcy but without strength and complexity. | 5 | 6 |
| | | Fresh but slightly dirty notes with anisic and artificial quality. When dried, woodiness developed but with earthy, slightly fishy and amine-like characters. An overall sweetness might suggest more suitable use in flavor. | 5 | 4 |

Structure I exhibited particularly desirable, strong and complex odors, superior to Structures II-VII. Its advantageous properties are unexpected.

What is claimed is:

1. A compound, 1-(2,4-dimethyl-cyclohex-3-enyl)-propan-1-ol.

2. A method of improving, enhancing or modifying a fragrance formulation through the addition of an olfactory acceptable amount of 1-(2,4-dimethyl-cyclohex-3-enyl)-propan-1-ol.

3. The method of claim 2, wherein the fragrance formulation is incorporated into a product selected from the group consisting of a perfume, a cologne, a toilet water, a cosmetic product, a personal care product, a fabric care product, a cleaning product, and an air freshener.

4. The method of claim 3, wherein the cleaning product is selected from the group consisting of a detergent, a dishwashing composition, a scrubbing compound, and a window cleaner.

5. The method of claim 2, wherein the olfactory acceptable amount is from about 0.005 to about 50 weight percent of the fragrance formulation.

6. The method of claim 2, wherein the olfactory acceptable amount is from about 0.1 to about 25 weight percent of the fragrance formulation.

7. The method of claim 2, wherein the olfactory acceptable amount is from about 0.5 to about 10 weight percent of the fragrance formulation.

8. A fragrance formulation containing an olfactory acceptable amount of 1-(2,4-dimethyl-cyclohex-3-enyl)-propan-1-ol.

9. A fragrance product containing an olfactory acceptable amount of the compound of claim 1.

* * * * *